United States Patent
Fukuyama et al.

(10) Patent No.: US 11,999,795 B2
(45) Date of Patent: Jun. 4, 2024

(54) MONOCLONAL ANTIBODY AND USE THEREOF

(71) Applicant: SCHOOL JURIDICAL PERSON THE KITASATO INSTITUTE, Tokyo (JP)

(72) Inventors: Takashi Fukuyama, Sagamihara (JP); Hitoshi Yamazaki, Sagamihara (JP); Mariko Ogi, Sagamihara (JP); Noritada Kobayashi, Sagamihara (JP); Yoshinobu Ichiki, Fukuoka (JP); Masahiko Hatakeyama, Tokyo (JP)

(73) Assignee: SCHOOL JURIDICAL PERSON THE KITASATO INSTITUTE, Tokyo (JP)

( * ) Notice: Subject to any disclaimer, the term of this patent is extended or adjusted under 35 U.S.C. 154(b) by 930 days.

(21) Appl. No.: 16/763,386

(22) PCT Filed: Nov. 9, 2018

(86) PCT No.: PCT/JP2018/041642
§ 371 (c)(1),
(2) Date: Dec. 2, 2020

(87) PCT Pub. No.: WO2019/098133
PCT Pub. Date: May 23, 2019

(65) Prior Publication Data
US 2021/0079110 A1    Mar. 18, 2021

(30) Foreign Application Priority Data
Nov. 14, 2017  (JP) .................................. 2017-218872

(51) Int. Cl.
  *G01N 33/53*  (2006.01)
  *C07K 16/30*  (2006.01)
  *G01N 33/574* (2006.01)

(52) U.S. Cl.
  CPC ........... *C07K 16/30* (2013.01); *G01N 33/574* (2013.01); *G01N 33/57492* (2013.01); *C07K 2317/565* (2013.01)

(58) Field of Classification Search
  CPC .............. C07K 16/30; C07K 2317/565; C07K 16/3069; C07K 16/32; G01N 33/574; G01N 33/57492; G01N 33/57446; C12N 5/12
  See application file for complete search history.

(56) References Cited

FOREIGN PATENT DOCUMENTS

| JP | 6028253 B2 | 10/2016 | |
|---|---|---|---|
| WO | WO2015014375 | * 2/2015 | ............. A61K 39/00 |
| WO | 2017/089756 | 6/2017 | |

OTHER PUBLICATIONS

Paret et al., "CXorf61 is a target for T cell based immunotherapy of triple-negative breast cancer," Oncotarget, Jul. 29, 2015, vol. 6, No. 28, p. 25356-25367.
Extended European Search Report dated Jul. 6, 2021 in European Application No. 18879444.0, 10 pages.
Anonymous: "Anti -CT83 antibody produced in rabbit Prestige Antibodies Powered by Atlas Antibodies, affinity isolated antibody, buffered aqueous glycerol solution : Sigma-Aldrich", May 3, 2006 (May 3, 2006), XP55805353. Retrieved from the internet: URL:https://www.sigmaaldrich.com/catalog/product/sigma/hpa004773?lang=en ion=NL.
Kondo Yasushi et al: "Detection of KK-LC-1 Protein, a Cancer/Testis Antigen, in Patients with Breast Cancer", Anticancer Research, vol. 38, No. 10, Oct. 2018 (Oct. 2018), pp. 5923-5928, XP009527565, ISSN: 0250-7005.
International Search Report for PCT/JP2018/041642, dated Jan. 29, 2019, 2 pages.
Written Opinion of the ISA for PCT/JP2018/041642, dated Jan. 29, 2019, 3 pages.
Paret et al., "CXorf61 is a target for T cell based immunotherapy of triple-negatice breast cancer", Oncotarget, Jul. 29, 2015, vol. 6, No. 28, pp. 25356-25367.
Yoshihito Takahashi, et al., "Expression of Kita-Kyushu Lung Cancer Antigen-1 as Detected by a Novel Monoclonal Antibody in Gastric Cancer", Anticancer Research, vol. 39, Issue 11, Nov. 2019, pp. 6259-6263.
Yoshinobu Ichiki, et al., "Relationship between Kita-Kyushu Lung Cancer antigen-1 expression and prognosis of cases with lung squamous cell carcinoma", Translational Cancer Research, vol. 10, No. 12, Dec. 2021, pp. 5212-5221.

* cited by examiner

*Primary Examiner* — Carmencita M Belei
(74) *Attorney, Agent, or Firm* — Nixon & Vanderhye P.C.

(57) ABSTRACT

Provided is a monoclonal antibody or a fragment thereof in which heavy-chain complementarity-determining regions (CDRs) 1 to 3 respectively consist of amino acid sequences of SEQ ID NOs: 2 to 4 and light-chain CDRs 1 to 3 respectively consist of amino acid sequences of SEQ ID NOs: 5 to 7; a monoclonal antibody or a fragment thereof in which heavy-chain CDRs 1 to 3 respectively consist of amino acid sequences obtained by deleting, substituting, or adding one or several amino acids in the amino acid sequences of SEQ ID NOs: 2 to 4 and light-chain CDRs 1 to 3 respectively consist of amino acid sequences obtained by deleting, substituting, or adding one or several amino acids in the amino acid sequences of SEQ ID NOs: 5 to 7, and which has binding properties to a KK-LC-1 protein; or a monoclonal antibody or a fragment thereof which competes with the monoclonal antibody or a fragment thereof in which the heavy-chain CDRs 1 to 3 respectively consist of the amino acid sequences of SEQ ID NOs: 2 to 4 and the light-chain CDRs 1 to 3 respectively consist of the amino acid sequences of SEQ ID NOs: 5 to 7, and has binding properties to the KK-LC-1 protein.

11 Claims, 6 Drawing Sheets

Specification includes a Sequence Listing.

(a)

(b)

(c)

(d)

(a)

(b)

(c)

(d)

SEQUENCE LISTING

<160> NUMBER OF SEQ ID NOS: 86

<210> SEQ ID NO 1
<211> LENGTH: 26
<212> TYPE: PRT
<213> ORGANISM: Homo sapiens

<400> SEQUENCE: 1

Glu Asn Lys Leu Val Glu Leu Glu His Thr Leu Leu Ser Lys Gly Phe
1               5                   10                  15

Arg Gly Ala Ser Pro His Arg Lys Ser Thr
            20                  25

<210> SEQ ID NO 2
<211> LENGTH: 5
<212> TYPE: PRT
<213> ORGANISM: Mus musculus

<400> SEQUENCE: 2

Glu Tyr Thr Met His
1               5

<210> SEQ ID NO 3
<211> LENGTH: 17
<212> TYPE: PRT
<213> ORGANISM: Mus musculus

<400> SEQUENCE: 3

Val Ile Tyr Pro Asn Asn Gly Asp Thr Ser Tyr Asn Gln Lys Phe Arg
1               5                   10                  15

Gly

<210> SEQ ID NO 4
<211> LENGTH: 8
<212> TYPE: PRT
<213> ORGANISM: Mus musculus

<400> SEQUENCE: 4

Leu Gly Trp Gln Gly Phe Ala Asn
1               5

<210> SEQ ID NO 5
<211> LENGTH: 16
<212> TYPE: PRT
<213> ORGANISM: Mus musculus

<400> SEQUENCE: 5

Arg Ser Ser Lys Ser Leu Leu His Ser Asn Gly Asn Thr Phe Leu Tyr
1               5                   10                  15

<210> SEQ ID NO 6
<211> LENGTH: 7
<212> TYPE: PRT
<213> ORGANISM: Mus musculus

<400> SEQUENCE: 6

Arg Met Ser Asn Leu Ala Ser
1               5

<210> SEQ ID NO 7
<211> LENGTH: 9
<212> TYPE: PRT
<213> ORGANISM: Mus musculus

<400> SEQUENCE: 7

Met Gln His Leu Glu Tyr Pro Leu Thr
1               5

<210> SEQ ID NO 8
<211> LENGTH: 136
<212> TYPE: PRT
<213> ORGANISM: Mus musculus

<400> SEQUENCE: 8

Met Gly Trp Ser Trp Ile Phe Leu Phe Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Thr Ser Gly Tyr Thr Ser
        35                  40                  45

Thr Glu Tyr Thr Met His Trp Val Lys Gln Ser His Gly Gln Ser Leu
    50                  55                  60

Glu Trp Ile Gly Val Ile Tyr Pro Asn Asn Gly Asp Thr Ser Tyr Asn
65                  70                  75                  80

Gln Lys Phe Arg Gly Lys Ala Thr Leu Thr Val Asp Lys Ser Ser Asn
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Trp Gln Gly Phe Ala Asn Trp Gly Gln
        115                 120                 125

Gly Thr Leu Val Thr Val Ser Ala
    130                 135

<210> SEQ ID NO 9
<211> LENGTH: 132
<212> TYPE: PRT
<213> ORGANISM: Mus musculus

<400> SEQUENCE: 9

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Phe Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Leu Thr Phe Gly Ala Gly Thr Lys
        115                 120                 125

Leu Glu Leu Lys
    130

<210> SEQ ID NO 10
<211> LENGTH: 408
<212> TYPE: DNA
<213> ORGANISM: Mus musculus

<400> SEQUENCE: 10
atgggatgga gctggatctt tctctttctc ctgtcaggaa ctgcaggtgt cctctctgag    60
gtccagctgc aacagtctgg acctgagctg gtgaagcctg ggcttcagt gaagatgtcc    120 tgcaagactt ctggatacac atccactgaa tacaccatgc actgggtgaa gcagagccat    180

```
ggacagagcc ttgagtggat tggagtcatt tatcctaaca atggtgatac tagctacaac    240
cagaagttca ggggcaaggc cacattgact gtggacaagt cctccaatac agcctacatg    300
gagctccgca gcctgacatc tgaggattct gcagtctatt actgtgcaag actgggctgg    360
caagggtttg ctaactgggg ccaagggact ctggtcactg tctctgca                 408
```

<210> SEQ ID NO 11
<211> LENGTH: 396
<212> TYPE: DNA
<213> ORGANISM: Mus musculus

<400> SEQUENCE: 11

```
atgaggtgcc tagctgagtt cctggggctg cttgtgctct ggatccctgg agccattggg     60
gatattgtga tgactcaggc tgcaccctct gtacctgtca ctcctggaga gtcagtatcc    120
atctcctgca ggtctagtaa gagtctcctg catagtaatg caacactttt cttgtattgg    180
ttcctgcaga ggccaggcca gtctcctcag ctcctgatat atcggatgtc caaccttgcc    240
tcaggagtcc cagacaggtt cagtggcagt gggtcaggaa ctgctttcac actgagaatc    300
agtagagtgg aggctgagga tgtgggtgtt tattactgta tgcaacatct agaatatccg    360
ctcacgttcg gtgctgggac caagctggag ctgaaa                             396
```

<210> SEQ ID NO 12
<211> LENGTH: 12
<212> TYPE: PRT
<213> ORGANISM: Artificial Sequence
<220> FEATURE:
<223> OTHER INFORMATION: Synthesyzed peptide derived from human

<400> SEQUENCE: 12

Asn Lys Leu Val Glu Leu Glu His Thr Leu Leu Ser
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 13

Gly Ser Gly Ser Gly Ser Gly Val Arg Pro Ser Ser Ser Gly Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 14

Ser Gly Ser Gly Ser Gly Val Arg Pro Ser Ser Ser Gly Leu Ile
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 15

Gly Ser Gly Ser Gly Val Arg Pro Ser Ser Ser Gly Leu Ile Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 16

Ser Gly Ser Gly Val Arg Pro Ser Ser Ser Gly Leu Ile Asn Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 17

Gly Ser Gly Val Arg Pro Ser Ser Ser Gly Leu Ile Asn Ser Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 18

Ser Gly Val Arg Pro Ser Ser Ser Gly Leu Ile Asn Ser Asn Thr
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 19

Gly Val Arg Pro Ser Ser Ser Gly Leu Ile Asn Ser Asn Thr Asp
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 20

Val Arg Pro Ser Ser Ser Gly Leu Ile Asn Ser Asn Thr Asp Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 21

Arg Pro Ser Ser Ser Gly Leu Ile Asn Ser Asn Thr Asp Asn Asn

```
1               5                   10                  15
```

<210> SEQ ID NO 22
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 22

```
Pro Ser Ser Ser Gly Leu Ile Asn Ser Asn Thr Asp Asn Asn Leu
1               5                   10                  15
```

<210> SEQ ID NO 23
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 23

```
Ser Ser Ser Gly Leu Ile Asn Ser Asn Thr Asp Asn Asn Leu Ala
1               5                   10                  15
```

<210> SEQ ID NO 24
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 24

```
Ser Ser Gly Leu Ile Asn Ser Asn Thr Asp Asn Asn Leu Ala Val
1               5                   10                  15
```

<210> SEQ ID NO 25
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 25

```
Ser Gly Leu Ile Asn Ser Asn Thr Asp Asn Asn Leu Ala Val Tyr
1               5                   10                  15
```

<210> SEQ ID NO 26
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 26

```
Gly Leu Ile Asn Ser Asn Thr Asp Asn Asn Leu Ala Val Tyr Asp
1               5                   10                  15
```

<210> SEQ ID NO 27
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 27

```
Leu Ile Asn Ser Asn Thr Asp Asn Asn Leu Ala Val Tyr Asp Leu
1               5                   10                  15
```

<210> SEQ ID NO 28
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 28

Ile Asn Ser Asn Thr Asp Asn Asn Leu Ala Val Tyr Asp Leu Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 29

Asn Ser Asn Thr Asp Asn Asn Leu Ala Val Tyr Asp Leu Ser Arg
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 30

Ser Asn Thr Asp Asn Asn Leu Ala Val Tyr Asp Leu Ser Arg Asp
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 31

Asn Thr Asp Asn Asn Leu Ala Val Tyr Asp Leu Ser Arg Asp Ile
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 32

Thr Asp Asn Asn Leu Ala Val Tyr Asp Leu Ser Arg Asp Ile Leu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 33

Asp Asn Asn Leu Ala Val Tyr Asp Leu Ser Arg Asp Ile Leu Asn
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 34

Asn Asn Leu Ala Val Tyr Asp Leu Ser Arg Asp Ile Leu Asn Asn
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 35

Asn Leu Ala Val Tyr Asp Leu Ser Arg Asp Ile Leu Asn Asn Phe
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 36

Leu Ala Val Tyr Asp Leu Ser Arg Asp Ile Leu Asn Asn Phe Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 37

Ala Val Tyr Asp Leu Ser Arg Asp Ile Leu Asn Asn Phe Pro His
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 38

Val Tyr Asp Leu Ser Arg Asp Ile Leu Asn Asn Phe Pro His Ser
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 39

Tyr Asp Leu Ser Arg Asp Ile Leu Asn Asn Phe Pro His Ser Ile
1               5                   10                  15

```
<210> SEQ ID NO 40
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 40

Asp Leu Ser Arg Asp Ile Leu Asn Asn Phe Pro His Ser Ile Ala
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 41

Leu Ser Arg Asp Ile Leu Asn Asn Phe Pro His Ser Ile Ala Arg
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 42

Ser Arg Asp Ile Leu Asn Asn Phe Pro His Ser Ile Ala Arg Gln
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 43

Arg Asp Ile Leu Asn Asn Phe Pro His Ser Ile Ala Arg Gln Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 44

Asp Ile Leu Asn Asn Phe Pro His Ser Ile Ala Arg Gln Lys Arg
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 45

Ile Leu Asn Asn Phe Pro His Ser Ile Ala Arg Gln Lys Arg Ile
1               5                   10                  15

<210> SEQ ID NO 46
```

```
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 46

Leu Asn Asn Phe Pro His Ser Ile Ala Arg Gln Lys Arg Ile Leu
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 47

Asn Asn Phe Pro His Ser Ile Ala Arg Gln Lys Arg Ile Leu Val
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 48

Asn Phe Pro His Ser Ile Ala Arg Gln Lys Arg Ile Leu Val Asn
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 49

Phe Pro His Ser Ile Ala Arg Gln Lys Arg Ile Leu Val Asn Leu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 50

Pro His Ser Ile Ala Arg Gln Lys Arg Ile Leu Val Asn Leu Ser
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 51

His Ser Ile Ala Arg Gln Lys Arg Ile Leu Val Asn Leu Ser Met
1               5                   10                  15

<210> SEQ ID NO 52
<211> LENGTH: 15
```

<212> TYPE: PRT
<213> ORGANISM: Artificial Sequence
<220> FEATURE:
<223> OTHER INFORMATION: Synthesyzed peptide derived from human

<400> SEQUENCE: 52

Ser Ile Ala Arg Gln Lys Arg Ile Leu Val Asn Leu Ser Met Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 53

Ile Ala Arg Gln Lys Arg Ile Leu Val Asn Leu Ser Met Val Glu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 54

Ala Arg Gln Lys Arg Ile Leu Val Asn Leu Ser Met Val Glu Asn
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 55

Arg Gln Lys Arg Ile Leu Val Asn Leu Ser Met Val Glu Asn Lys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 56

Gln Lys Arg Ile Leu Val Asn Leu Ser Met Val Glu Asn Lys Leu
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 57

Lys Arg Ile Leu Val Asn Leu Ser Met Val Glu Asn Lys Leu Val
1               5                   10                  15

<210> SEQ ID NO 58
<211> LENGTH: 15
<212> TYPE: PRT

<213> ORGANISM: Artificial Sequence
<220> FEATURE:
<223> OTHER INFORMATION: Synthesyzed peptide derived from human

<400> SEQUENCE: 58

Arg Ile Leu Val Asn Leu Ser Met Val Glu Asn Lys Leu Val Glu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 59

Ile Leu Val Asn Leu Ser Met Val Glu Asn Lys Leu Val Glu Leu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 60

Leu Val Asn Leu Ser Met Val Glu Asn Lys Leu Val Glu Leu Glu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 61

Val Asn Leu Ser Met Val Glu Asn Lys Leu Val Glu Leu Glu His
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 62

Asn Leu Ser Met Val Glu Asn Lys Leu Val Glu Leu Glu His Thr
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 63

Leu Ser Met Val Glu Asn Lys Leu Val Glu Leu Glu His Thr Leu
1               5                   10                  15

<210> SEQ ID NO 64
<211> LENGTH: 15
<212> TYPE: PRT
<213> ORGANISM: Artificial Sequence

```
<220> FEATURE:
<223> OTHER INFORMATION: Synthesyzed peptide derived from human

<400> SEQUENCE: 64

Ser Met Val Glu Asn Lys Leu Val Glu Leu Glu His Thr Leu Leu
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 65

Met Val Glu Asn Lys Leu Val Glu Leu Glu His Thr Leu Leu Ser
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 66

Val Glu Asn Lys Leu Val Glu Leu Glu His Thr Leu Leu Ser Lys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 67

Glu Asn Lys Leu Val Glu Leu Glu His Thr Leu Leu Ser Lys Gly
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 68

Asn Lys Leu Val Glu Leu Glu His Thr Leu Leu Ser Lys Gly Phe
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 69

Lys Leu Val Glu Leu Glu His Thr Leu Leu Ser Lys Gly Phe Arg
1               5                   10                  15

<210> SEQ ID NO 70
<211> LENGTH: 15
<212> TYPE: PRT
<213> ORGANISM: Artificial Sequence
<220> FEATURE:
```

```
<223> OTHER INFORMATION: Synthesyzed peptide derived from human

<400> SEQUENCE: 70

Leu Val Glu Leu Glu His Thr Leu Leu Ser Lys Gly Phe Arg Gly
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 71

Val Glu Leu Glu His Thr Leu Leu Ser Lys Gly Phe Arg Gly Ala
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 72

Glu Leu Glu His Thr Leu Leu Ser Lys Gly Phe Arg Gly Ala Ser
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 73

Leu Glu His Thr Leu Leu Ser Lys Gly Phe Arg Gly Ala Ser Pro
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 74

Glu His Thr Leu Leu Ser Lys Gly Phe Arg Gly Ala Ser Pro His
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 75

His Thr Leu Leu Ser Lys Gly Phe Arg Gly Ala Ser Pro His Arg
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthesyzed peptide derived from human
```

<400> SEQUENCE: 76

Thr Leu Leu Ser Lys Gly Phe Arg Gly Ala Ser Pro His Arg Lys
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 77

Leu Leu Ser Lys Gly Phe Arg Gly Ala Ser Pro His Arg Lys Ser
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 78

Leu Ser Lys Gly Phe Arg Gly Ala Ser Pro His Arg Lys Ser Thr
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 79

Ser Lys Gly Phe Arg Gly Ala Ser Pro His Arg Lys Ser Thr Gly
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 80

Lys Gly Phe Arg Gly Ala Ser Pro His Arg Lys Ser Thr Gly Ser
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 81

Gly Phe Arg Gly Ala Ser Pro His Arg Lys Ser Thr Gly Ser Gly
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthesyzed peptide derived from human

```
<400> SEQUENCE: 82

Phe Arg Gly Ala Ser Pro His Arg Lys Ser Thr Gly Ser Gly Ser
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 83

Arg Gly Ala Ser Pro His Arg Lys Ser Thr Gly Ser Gly Ser Gly
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 84

Gly Ala Ser Pro His Arg Lys Ser Thr Gly Ser Gly Ser Gly Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthesyzed peptide derived from human

<400> SEQUENCE: 85

Ala Ser Pro His Arg Lys Ser Thr Gly Ser Gly Ser Gly Ser Gly
1               5                   10                  15

<210> SEQ ID NO 86
<211> LENGTH: 113
<212> TYPE: PRT
<213> ORGANISM: Homo sapiens

<400> SEQUENCE: 86

Met Asn Phe Tyr Leu Leu Leu Ala Ser Ser Ile Leu Cys Ala Leu Ile
1               5                   10                  15

Val Phe Trp Lys Tyr Arg Arg Phe Gln Arg Asn Thr Gly Glu Met Ser
            20                  25                  30

Ser Asn Ser Thr Ala Leu Ala Leu Val Arg Pro Ser Ser Ser Gly Leu
        35                  40                  45

Ile Asn Ser Asn Thr Asp Asn Asn Leu Ala Val Tyr Asp Leu Ser Arg
    50                  55                  60

Asp Ile Leu Asn Asn Phe Pro His Ser Ile Ala Arg Gln Lys Arg Ile
65                  70                  75                  80

Leu Val Asn Leu Ser Met Val Glu Asn Lys Leu Val Glu Leu Glu His
                85                  90                  95

Thr Leu Leu Ser Lys Gly Phe Arg Gly Ala Ser Pro His Arg Lys Ser
            100                 105                 110

Thr
```

MONOCLONAL ANTIBODY AND USE THEREOF

This application is the U.S. national phase of International Application No. PCT/JP2018/041642 filed 9 Nov. 2018, which designated the U.S. and claims priority to JP Patent Application No. 2017-218872 filed 14 Nov. 2017, the entire contents of each of which are hereby incorporated by reference.

TECHNICAL FIELD

The present invention relates to a monoclonal antibody and use thereof. More specifically, the present invention relates to a monoclonal antibody or a fragment thereof, a cancer detection kit, a cancer detection method, and a hybridoma cell line. Priority is claimed on Japanese Patent Application No. 2017-218872, filed Nov. 14, 2017, the content of which is incorporated herein by reference.

BACKGROUND ART

It is becoming clear that Kitakyushu lung cancer antigen-1 (KK-LC-1) can be used as a marker expressed in various cancers (for example, see Patent Literature 1). Therefore, it is important to develop a technique capable of easily detecting KK-LC-1.

CITATION LIST

Patent Literature

[Patent Literature 1]
Japanese Patent No. 6028253

SUMMARY OF INVENTION

Technical Problem

An object of the present invention is to provide a technique for easily detecting KK-LC-1.

Solution to Problem

The present invention includes the following aspects.
[1] A monoclonal antibody or a fragment thereof, which is one of the following (i) to (iii).
 (i) A monoclonal antibody or a fragment thereof in which heavy-chain complementarity-determining regions (CDRs) 1 to 3 respectively consist of amino acid sequences of SEQ ID NOs: 2 to 4 and light-chain CDRs 1 to 3 respectively consist of amino acid sequences of SEQ ID NOs: 5 to 7
 (ii) A monoclonal antibody or a fragment thereof in which heavy-chain CDRs 1 to 3 respectively consist of amino acid sequences obtained by deleting, substituting, or adding one or several amino acids in the amino acid sequences of SEQ ID NOs: 2 to 4 and light-chain CDRs 1 to 3 respectively consist of amino acid sequences obtained by deleting, substituting, or adding one or several amino acids in the amino acid sequences of SEQ ID NOs: 5 to 7, and which has binding properties to a KK-LC-1 protein
 (iii) A monoclonal antibody or a fragment thereof which competes with the monoclonal antibody or a fragment thereof in which the heavy-chain CDRs 1 to 3 respectively consist of the amino acid sequences of SEQ ID NOs: 2 to 4 and the light-chain CDRs 1 to 3 respectively consist of the amino acid sequences of SEQ ID NOs: 5 to 7, and has binding properties to the KK-LC-1 protein
[2] The monoclonal antibody or a fragment thereof as described in [1], in which the monoclonal antibody or a fragment thereof has binding properties to a KK-LC-1 protein in a fixed biological sample.
[3] The monoclonal antibody or a fragment thereof as described in [2], in which the biological sample is fixed with a crosslinking fixative. [4] The monoclonal antibody or a fragment thereof as described in [3], in which the crosslinking fixative is formaldehyde, paraformaldehyde, or glutaraldehyde.
[5] The monoclonal antibody or a fragment thereof as described in any one of [1] to [4], in which the monoclonal antibody or a fragment thereof has binding properties to a peptide consisting of an amino acid sequence set forth in SEQ ID NO: 1.
[6] The monoclonal antibody or a fragment thereof as described in any one of [1] to [5], in which the monoclonal antibody or a fragment thereof has binding properties to a peptide consisting of an amino acid sequence set forth in SEQ ID NO: 12.
[7] The monoclonal antibody or a fragment thereof as described in any one of [1] to [6], in which the monoclonal antibody or a fragment thereof is produced by a hybridoma cell line having an accession number of NITE BP-02527.
[8] A cancer detection kit including the monoclonal antibody or a fragment thereof as described in any one of [1] to [7].
[9] A nucleic acid encoding the monoclonal antibody or a fragment thereof as described in any one of [1] to [7].
[10] A cancer detection method including a step of reacting a fixed biological sample with the monoclonal antibody or a fragment thereof as described in any one of [1] to [7].
[11] A hybridoma cell line having an accession number of NITE BP-02527.
[12] A method for detecting a KK-LC-1 protein in a biological sample, including a step of detecting a peptide consisting of an amino acid sequence set forth in SEQ ID NO: 1 or a partial peptide thereof.
[13] The method as described in [12], wherein the partial peptide is a peptide consisting of an amino acid sequence set forth in SEQ ID NO: 12.

Advantageous Effects of Invention

According to the present invention, it is possible to provide a technique for easily detecting KK-LC-1. The present invention makes it possible to detect the expression of the KK-LC-1 by immunohistochemical staining, for example. Moreover, an anti-KK-LC-1 monoclonal antibody can be semipermanently supplied, and thus can be suitably used as a diagnostic agent.

Figure 3:
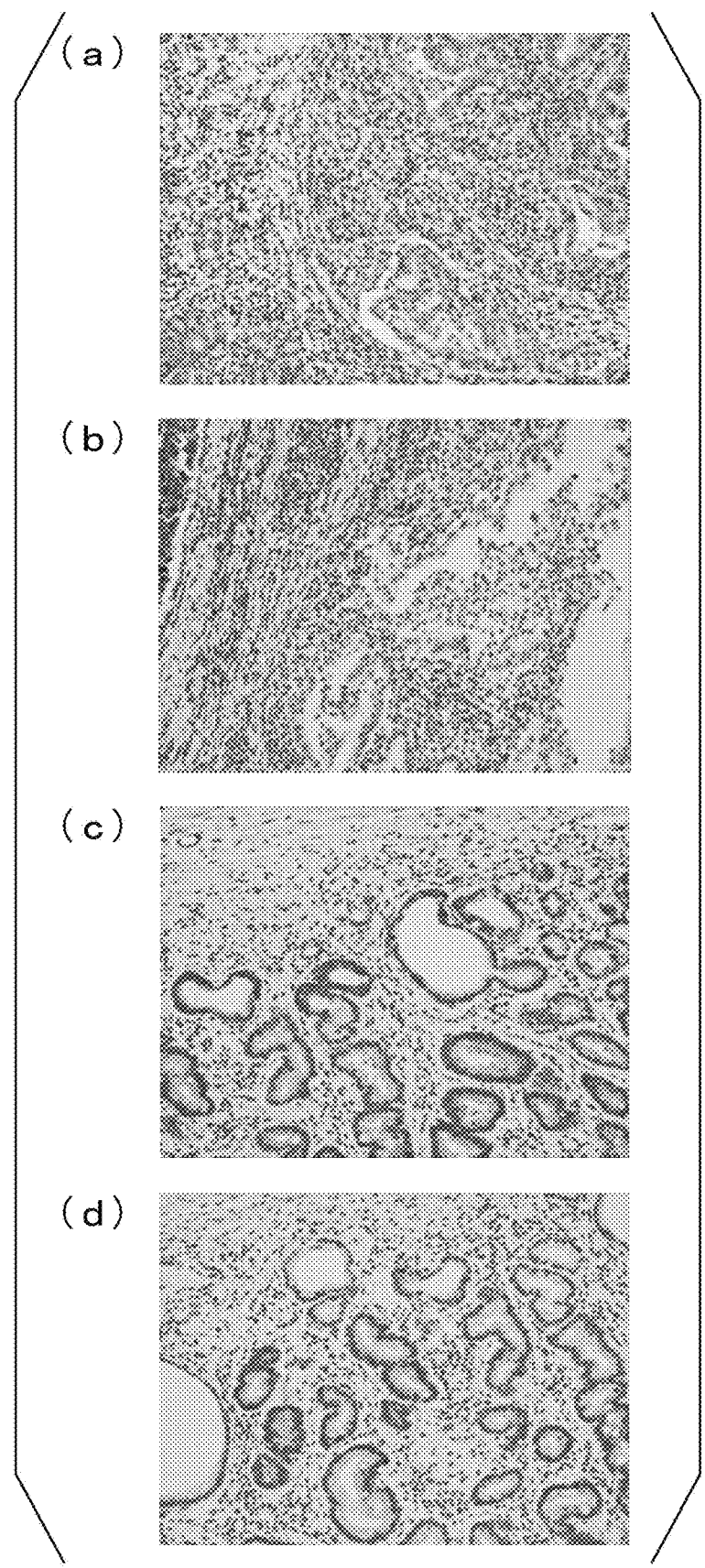

(a) to (d) of FIG. 3 are photographs showing results of immunohistochemical staining in Experimental Example 4.

Figure 4:
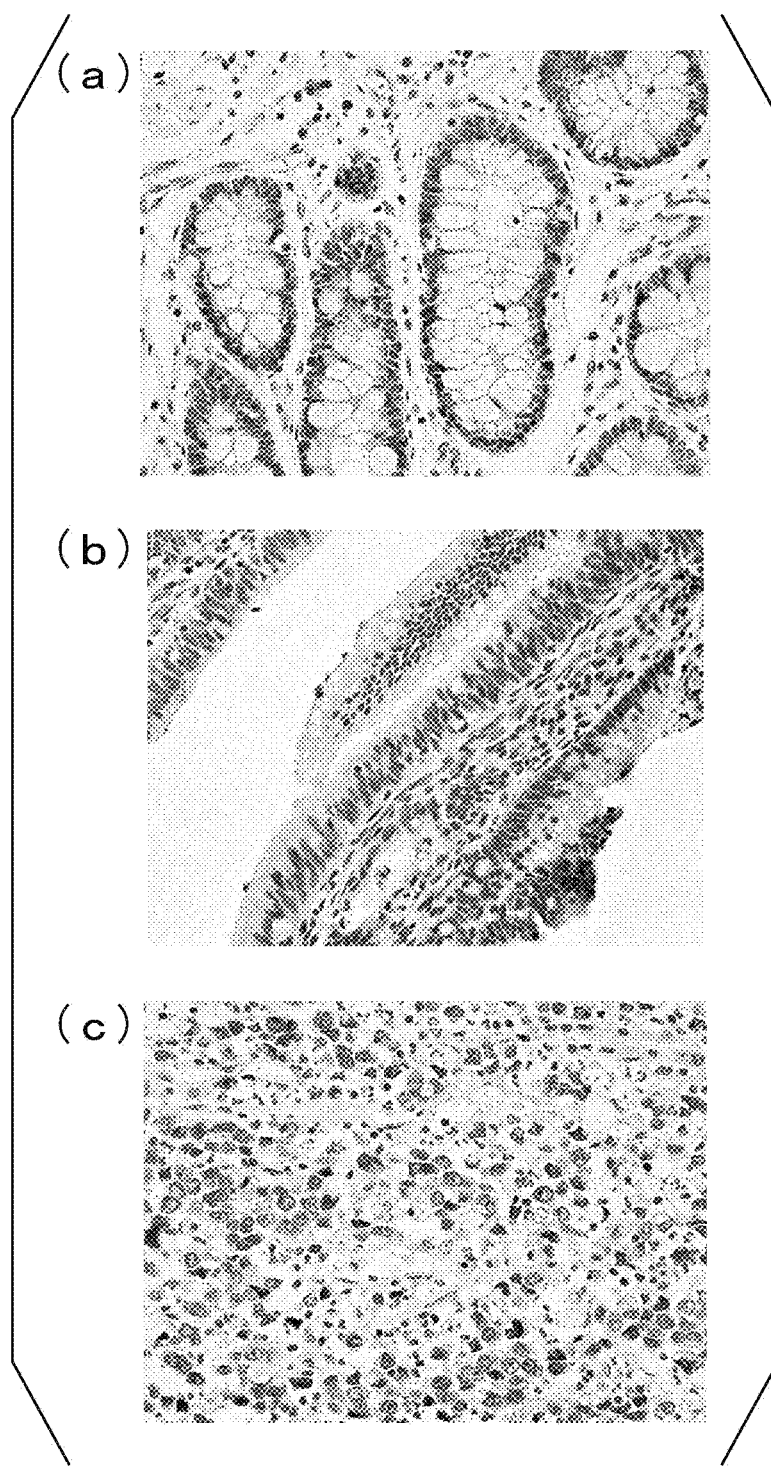

(a) to (c) of FIG. 4 are photographs showing results of immunohistochemical staining in Experimental Example 5.

Figure 5:
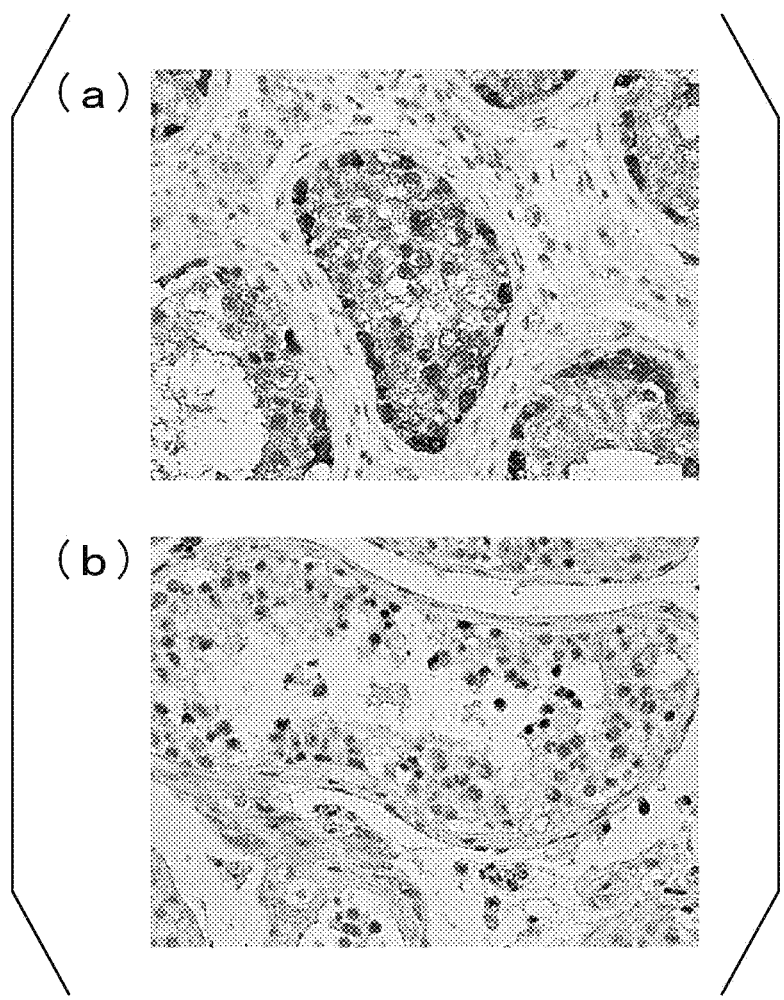

(a) and (b) of FIG. 5 are photographs showing results of immunohistochemical staining in Experimental Example 6.

Figure 6:
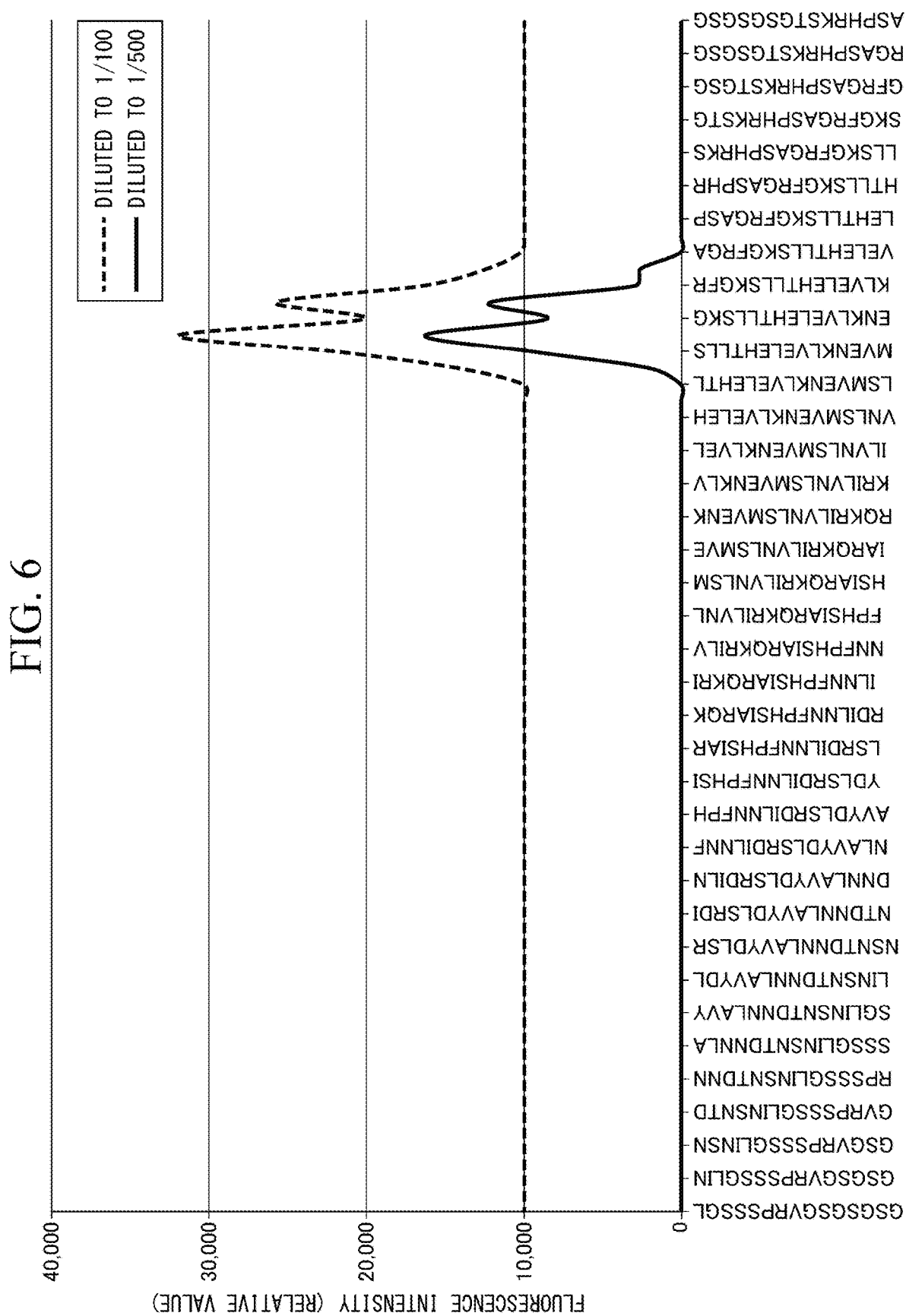

FIG. 6 is a graph showing results of epitope flapping in Experimental Example 8.

DESCRIPTION OF EMBODIMENTS

[Monoclonal Antibody or Fragment Thereof]

In one embodiment, the present invention provides a monoclonal antibody or a fragment thereof, which has binding properties to a KK-LC-1 protein in a fixed biological sample. It was difficult to obtain such a hybridoma cell line, but as will be described later in Examples, the present inventors have succeeded in establishing a hybridoma cell line which produces a monoclonal antibody capable of reacting with a KK-LC-1 protein in a fixed biological sample. An NCBI accession number of the KK-LC-1 protein is NP_001017978.1, and an amino acid sequence thereof is shown in SEQ ID NO: 86.

In the present specification, examples of the fragment of the monoclonal antibody include antibody fragments known in the related art, and more specific examples thereof include F(ab')2, Fab', Fab, Fv, and scFv.

The monoclonal antibody or a fragment thereof according to the present embodiment may be obtained by immunizing an animal, or may be obtained by screening using a phage library or the like. Moreover, the monoclonal antibody or a fragment thereof according to the present embodiment may be produced from a hybridoma cell line described later, or may be a gene recombinant. A host of the gene recombinant is not particularly limited, and may be, for example, a microorganism such as *Escherichia coli* and yeast, an insect cell, a plant cell, an animal cell, or the like.

The monoclonal antibody or a fragment thereof according to the present embodiment can be suitably used for immunohistochemical staining, for example. In the related art, an anti-KK-LC-1 monoclonal antibody which can be used for immunohistochemical staining was not present. Since the monoclonal antibody or a fragment thereof according to the present embodiment can be semipermanently supplied and quality control is also easy, the monoclonal antibody or a fragment thereof can be used as a diagnostic agent, for example.

In the present embodiment, the fixed biological sample is preferably a biological sample fixed with a crosslinking fixative. That is, the KK-LC-1 protein to be detected by the monoclonal antibody or a fragment thereof according to the present embodiment is preferably present in the biological sample fixed with the crosslinking fixative. The monoclonal antibody or a fragment thereof according to the present embodiment can be satisfactorily reacted even with the KK-LC-1 protein in such a biological sample. As described above, in the related art, an anti-KK-LC-1 monoclonal antibody which can be used for immunohistochemical staining of the fixed biological sample was not present. Here, examples of the crosslinking fixative include formaldehyde, paraformaldehyde, and glutaraldehyde.

The monoclonal antibody or a fragment thereof according to the present embodiment is preferably produced by a hybridoma cell line having an accession number of NITE BP-02527. Furthermore, the monoclonal antibody or a fragment thereof produced by the hybridoma cell line having an accession number of NITE BP-02527 has binding properties not only to the KK-LC-1 protein in the fixed biological sample but also to a KK-LC-1 protein in a non-fixed biological sample.

The monoclonal antibody or a fragment thereof according to the present embodiment preferably has binding properties to a peptide consisting of an amino acid sequence set forth in SEQ ID NO: 1. As will be described later in Examples, the monoclonal antibody produced by the hybridoma cell line having an accession number of NITE BP-02527 has binding properties to the peptide consisting of the amino acid sequence set forth in SEQ ID NO: 1.

The monoclonal antibody or a fragment thereof according to the present embodiment more preferably has binding properties to a peptide consisting of an amino acid sequence set forth in SEQ ID NO: 12. As will be described later in Examples, the present inventors have identified an epitope recognized by a monoclonal antibody through epitope mapping. As a result, it was found that the monoclonal antibody produced by the hybridoma cell line having an accession number of NITE BP-02527 has binding properties to the peptide consisting of the amino acid sequence set forth in SEQ ID NO: 12. Furthermore, as will be described later, the monoclonal antibody may have binding properties even to a peptide in which a serine residue at a C-terminus, an asparagine residue at an N-terminus, or the asparagine residue at the N-terminus and a second lysine residue from the N-terminus are deleted in the amino acid sequence set forth in SEQ ID NO: 12.

The monoclonal antibody or a fragment thereof according to the present embodiment may be any one of the following (i) to (iii).

(i) A monoclonal antibody or a fragment thereof in which heavy-chain complementarity-determining regions (CDRs) 1 to 3 respectively consist of amino acid sequences of SEQ ID NOs: 2 to 4 and light-chain CDRs 1 to 3 respectively consist of amino acid sequences of SEQ ID NOs: 5 to 7

(ii) A monoclonal antibody or a fragment thereof in which heavy-chain CDRs 1 to 3 respectively consist of amino acid sequences obtained by deleting, substituting, or adding one or several amino acids in the amino acid sequences of SEQ ID NOs: 2 to 4 and light-chain CDRs 1 to 3 respectively consist of amino acid sequences obtained by deleting, substituting, or adding one or several amino acids in the amino acid sequences of SEQ ID NOs: 5 to 7, and which has binding properties to a KK-LC-1 protein (iii) A monoclonal antibody or a fragment thereof which competes with the monoclonal antibody or a fragment thereof in which the heavy-chain CDRs 1 to 3 respectively consist of the amino acid sequences of SEQ ID NOs: 2 to 4 and the light-chain CDRs 1 to 3 respectively consist of the amino acid sequences of SEQ ID NOs: 5 to 7, and has binding properties to the KK-LC-1 protein SEQ ID NOs: 2 to 4 are respectively amino acid sequences of the heavy-chain CDRs 1 to 3 of the monoclonal antibody produced by the hybridoma cell line having an accession number of NITE BP-02527. Moreover, SEQ ID NOs: 5 to 7 are respectively amino acid sequences of the light-chain CDRs 1 to 3 of the monoclonal antibody produced by the hybridoma cell line having an accession number of NITE BP-02527.

That is, the monoclonal antibody or a fragment thereof according to the present embodiment may have the same heavy-chain CDRs 1 to 3 and the same light-chain CDRs 1 to 3 as those of the monoclonal antibody produced by the hybridoma cell line having an accession number of NITE BP-02527.

Alternatively, as long as the monoclonal antibody or a fragment thereof according to the present embodiment has binding properties to the KK-LC-1 protein in the fixed biological sample, the monoclonal antibody or a fragment thereof may have heavy-chain CDRs 1 to 3 and light-chain CDRs 1 to 3 which have mutations with respect to the heavy-chain CDRs 1 to 3 and the light-chain CDRs 1 to 3 of the monoclonal antibody produced by the hybridoma cell line having an accession number of NITE BP-02527.

That is, the monoclonal antibody or a fragment thereof according to the present embodiment may be a monoclonal antibody or a fragment thereof in which heavy-chain CDRs 1 to 3 respectively have amino acid sequences obtained by deleting, substituting, or adding one or several amino acids in the amino acid sequences of SEQ ID NOs: 2 to 4 and light-chain CDRs 1 to 3 respectively have amino acid sequences obtained by deleting, substituting, or adding one or several amino acids in the amino acid sequences of SEQ ID NOs: 5 to 7.

Here, the number of one or several amino acids may be, for example, 1 to 10, may be, for example, 1 to 5, or may be, for example, 1 to 3.

The monoclonal antibody or a fragment thereof according to the present embodiment may have a heavy-chain variable region having an amino acid sequence set forth in SEQ ID NO: 8 and a light-chain variable region having an amino acid sequence set forth in SEQ ID NO: 9.

Alternatively, the monoclonal antibody or a fragment thereof according to the present embodiment may be a monoclonal antibody or a fragment thereof which competes with the monoclonal antibody or a fragment thereof produced by the hybridoma cell line having an accession number of NITE BP-02527, and has binding properties to the KK-LC-1 protein.

Here, "the target antibody competes" means that for example, when the KK-LC-1 protein is reacted with the monoclonal antibody produced by the hybridoma cell line having an accession number of NITE BP-02527 and then reacted with the target antibody, at least part of binding between the monoclonal antibody produced by the hybridoma cell line having an accession number of NITE BP-02527 and the KK-LC-1 protein is dissociated and the target antibody is bound to the KK-LC-1 protein.

Here, at least part may be meant to be 10% or more, 30% or more, 50% or more, 70% or more, or 90% or more with respect to the number of moles of the KK-LC-1 protein.

The monoclonal antibody or a fragment thereof according to the present embodiment may be humanized. Examples of a human-type antibody include a chimeric antibody, a humanized antibody, and a fully human antibody. Here, the chimeric antibody means an antibody in which a variable region is an antibody derived from a non-human animal and at least part of a constant region is an antibody derived from a human being. Moreover, the humanized antibody means an antibody in which only complementarity determining regions of a heavy chain and a light chain are antibodies derived from a non-human animal and a constant region and a framework region are antibodies derived from a human being. Furthermore, the fully human antibody means that the entire region including complementarity determining regions is an antibody derived from a human being. In a case where the monoclonal antibody or a fragment thereof is the human-type antibody or a fragment thereof, the monoclonal antibody or a fragment thereof has low immunogenicity even when administered to a human being, and thus a side effect such as anaphylactic shock can be suppressed. Therefore, when the monoclonal antibody or a fragment thereof according to the present embodiment is the human-type antibody or a fragment thereof, the monoclonal antibody or a fragment thereof can be administered to a human being.

[Nucleic Acid]

In one embodiment, the present invention provides a nucleic acid encoding the above-described monoclonal antibody or a fragment thereof.

The nucleic acid according to the present embodiment preferably encodes a monoclonal antibody or a fragment thereof in which heavy-chain CDRs 1 to 3 respectively have the amino acid sequences of SEQ ID NOs: 2 to 4 or amino acid sequences obtained by deleting, substituting, or adding one or several amino acids in the amino acid sequences of SEQ ID NOs: 2 to 4 and light-chain CDRs 1 to 3 respectively have the amino acid sequences of SEQ ID NOs: 5 to 7 or amino acid sequences obtained by deleting, substituting, or adding one or several amino acids in the amino acid sequences of SEQ ID NOs: 5 to 7, and which has binding properties to the KK-LC-1 protein in the fixed biological sample.

The nucleic acid according to the present embodiment may be a nucleic acid in which a base sequence of a heavy-chain variable region gene has a base sequence of SEQ ID NO: 10 and a base sequence of a light-chain variable region gene has a base sequence of SEQ ID NO: 11. Alternatively, the nucleic acid according to the present embodiment may have a mutation as long as the monoclonal antibody or a fragment thereof to be encoded has binding properties to the KK-LC-1 protein in the fixed biological sample.

That is, the nucleic acid according to the present embodiment may be a nucleic acid in which a base sequence of a heavy-chain variable region gene has a sequence identity of 80% or more, preferably 90% or more, more preferably 95% or more, and still more preferably 99% or more with the base sequence of SEQ ID NO: 10 and a base sequence of a light-chain variable region gene has a sequence identity of 80% or more, preferably 90% or more, more preferably 95% or more, and still more preferably 99% or more with the base sequence of SEQ ID NO: 11.

Here, a sequence identity of a target base sequence with respect to a reference base sequence can be determined as follows, for example. First, the reference base sequence and the target base sequence are aligned. Here, each base sequence may include a gap so as to maximize the sequence identity. Subsequently, the number of matched bases in the reference base sequence and the target base sequence is calculated, and the sequence identity can be determined according to Expression (1).

$$\text{Sequence identity (\%)} = \text{number of matched bases}/\text{total number of bases in target base sequence} \times 100 \qquad (1)$$

The nucleic acid according to the present embodiment may be contained in a vector. Moreover, the vector may be an expression vector capable of expressing the above-described monoclonal antibody or a fragment thereof. Furthermore, the vector may be introduced into a host, for example, a microorganism such as *Escherichia coli* and yeast, an insect cell, a plant cell, and an animal cell. That is, in one embodiment, the present invention provides a host into which the vector is introduced.

[Cancer Detection Kit]

In one embodiment, the present invention provides a cancer detection kit including the above-described monoclonal antibody or a fragment thereof. According to the kit of the present embodiment, a cancer can be easily detected by immunohistochemical staining of a fixed biological sample. Examples of the fixed biological sample include the same fixed biological sample as those described above, and for example, a thin sliced section of fixed tissue may be used.

Examples of a cancer to be detected by the kit according to the present embodiment include a gastric cancer, a lung cancer, a breast cancer, a colon cancer, an esophageal cancer, a pancreatic cancer, a biliary tract cancer, a gallbladder cancer, a duodenal cancer, a colon cancer, a liver cancer, a brain tumor, a uterine cancer, an ovarian cancer, a leukemia, an osteosarcoma, a mesothelioma, a testicular tumor, and a gastrointestinal stromal tumor.

[Cancer Detection Method]

In one embodiment, the present invention provides a cancer detection method including a step of reacting a fixed biological sample with the above-described monoclonal antibody or a fragment thereof. The detection method according to the present embodiment can be said to be a data collection method for diagnosing whether or not a subject suffers from a cancer. Furthermore, the data collection method does not include a step of a determination by a doctor.

When a KK-LC-1 protein is detected in a fixed biological sample by the detection method according to the present embodiment, it can be determined that application of a cancer treatment targeting KK-LC-1 is effective for a patient from which the biological sample is derived.

Examples of a cancer to be detected by the method according to the present embodiment include a gastric cancer, a lung cancer, a breast cancer, a colon cancer, an esophageal cancer, a pancreatic cancer, a biliary tract cancer, a gallbladder cancer, a duodenal cancer, a colon cancer, a liver cancer, a brain tumor, a uterine cancer, an ovarian cancer, a leukemia, an osteosarcoma, a mesothelioma, a testicular tumor, and a gastrointestinal stromal tumor.

A cancer can be easily detected by the method according to the present embodiment. The method according to the present embodiment can be realized by the above-described monoclonal antibody or a fragment thereof.

[Hybridoma Cell Line]

In one embodiment, the present invention provides a hybridoma cell line having an accession number of NITE BP-02527. By culturing the hybridoma cell line according to the present embodiment, the above-described monoclonal antibody can be produced. Moreover, an antibody fragment can be obtained by cleaving the produced monoclonal antibody with pepsin or papain or the like.

[Method for Detecting KK-LC-1 Protein in Biological Sample]

In one embodiment, the present invention provides a method for detecting a KK-LC-1 protein in a biological sample, including a step of detecting a peptide consisting of the amino acid sequence set forth in SEQ ID NO: 1 or a partial peptide thereof. Moreover, the partial peptide is preferably a peptide consisting of the amino acid sequence set forth in SEQ ID NO: 12. According to the method of the present embodiment, even a KK-LC-1 protein in a fixed biological sample can be detected.

Incidentally, the peptide consisting of the amino acid sequence set forth in SEQ ID NO: 12 corresponds to the 89th to 100th amino acids of the KK-LC-1 protein of which amino acid sequence is shown in SEQ ID NO: 86. Moreover, a peptide consisting of the 80th to 101st amino acids of the KK-LC-1 protein is known to be secreted into blood. Therefore, the partial peptide of the KK-LC-1 protein secreted in the blood can be detected by detecting the peptide consisting of the amino acid sequence set forth in SEQ ID NO: 12.

Another Embodiment

In one embodiment, the present invention provides a cancer treatment method including a step of reacting a fixed biological sample derived from a patient with the above-described monoclonal antibody or a fragment thereof and a step of applying a cancer treatment targeting KK-LC-1 to the patient when the KK-LC-1 protein is detected in the biological sample.

Examples of the cancer treatment targeting KK-LC-1 include cancer immunotherapy using the KK-LC-1 protein as a cancer antigen and a molecular targeted therapy targeting the KK-LC-1 protein expressed on a cell membrane. The molecular targeted therapy may be a therapy using an antibody drug which recognizes the KK-LC-1 protein.

EXAMPLES

Experimental Example 1

(Establishment of Hybridoma Cell Line)

A mouse was immunized with a peptide having an amino acid sequence set forth in SEQ ID NO: 1, and about 30 clones of a hybridoma cell line were established.

Experimental Example 2

(Confirmation of Reactivity of Monoclonal Antibody by ELISA Method)

Reactivity of a monoclonal antibody was confirmed by an ELISA method using an immunized peptide as an antigen. Specifically, first, the peptide having the amino acid sequence set forth in SEQ ID NO: 1 was immobilized on a 96-well plate. Moreover, as a control, a 96-well plate in which only blocking was performed without immobilizing the peptide was used. A skim milk solution was used for the blocking.

Subsequently, the 96-well plate was blocked, a culture supernatant of each established hybridoma cell line was added thereto, and a reaction was performed. Moreover, for comparison, wells reacted with a normal mouse serum were also prepared. Next, the unreacted monoclonal antibody was washed off, the resultant was reacted with an anti-mouse secondary antibody, and a chromogenic substrate was added to develop color. Then, absorbance of each well was measured using a plate reader.

Figure 1:
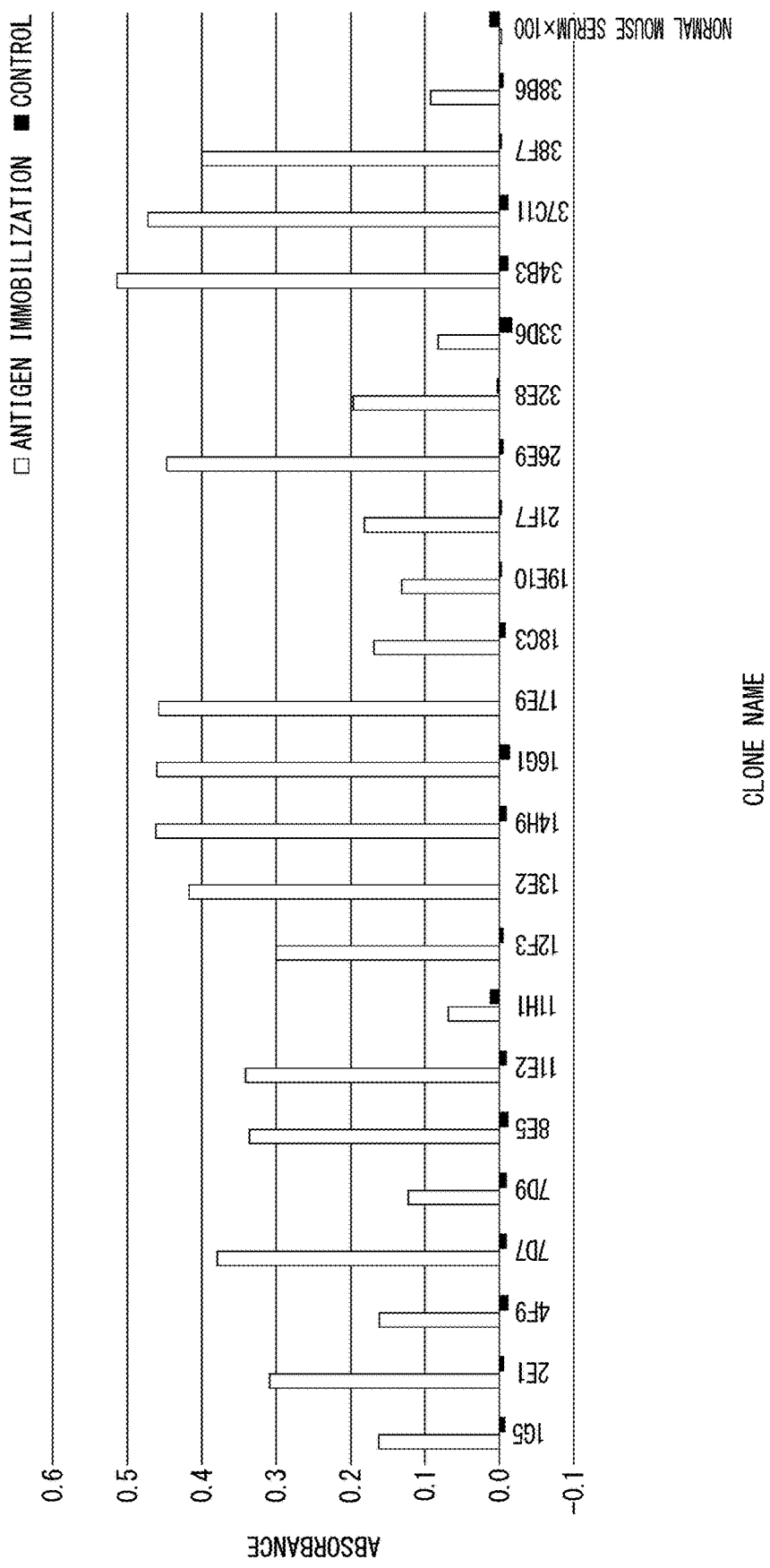
FIG. 1 is a graph showing results of Experimental Example 2.
 (a) to (d) of FIG. 2 are photographs showing results of immunohistochemical staining in Experimental Example 3.

FIG. 1 is a graph showing results of measuring reactivity of monoclonal antibodies by the ELISA method. In FIG. 1, a horizontal axis indicates clone names of the hybridoma cell line. The clone name of "34B3" is the hybridoma cell line having the accession number of NITE BP-02527.

As a result, it was confirmed that a large number of monoclonal antibodies showing reactivity to the KK-LC-1 protein in the ELISA method were obtained.

Experimental Example 3

(Confirmation 1 of Reactivity of Monoclonal Antibody by Immunohistochemical Staining)

Tissue slices of a normal region and a tumor region of a patient suffering from a testicular tumor and tissue slices of a normal region and a tumor region in a gastric tissue of a patient suffering from a gastric cancer, which are fixed with formaldehyde, were stained by using the produced monoclonal antibodies. As a result, it was found that only the monoclonal antibody produced by one clone among the established about 30 clones of the hybridoma cell line could stain the KK-LC-1 protein in immunohistochemical staining after a pretreatment for activation by an autoclave.

The hybridoma cell line which produced the monoclonal antibody capable of staining the KK-LC-1 protein in immunohistochemical staining was domestically deposited with the National Institute of Technology and Evaluation (2-5-8 Kazusakamatari, Kisarazu-shi, Chiba) (accession date: Aug. 3, 2017, accession number: NITE P-02527, cell name of "277 34B3 20170123"). Thereafter, the hybridoma cell line (accession number: NITE P-02527) was transferred to international deposit (international depositary authority: the National Institute of Technology and Evaluation (2-5-8 Kazusakamatari, Kisarazu-shi, Chiba), accession date: Oct. 10, 2018, accession number: NITE BP-02527, cell name of "277 34B3 20170123").

Figure 2:
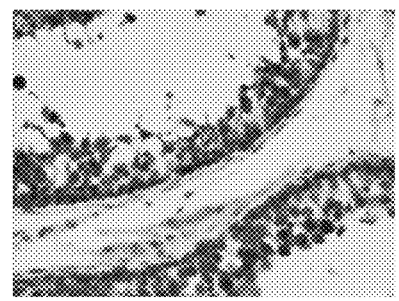
Figure 2:
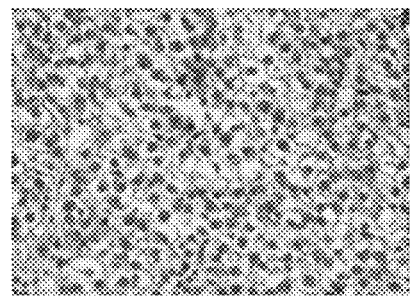
Figure 2:
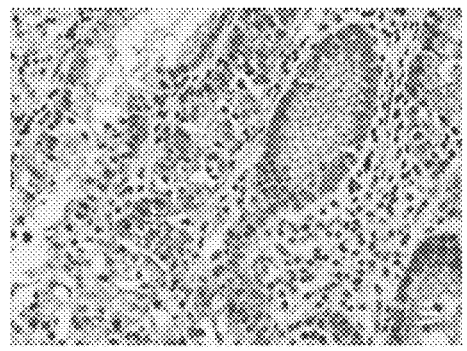
Figure 2:
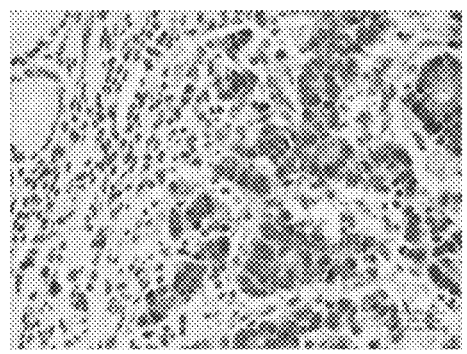

(a) to (d) of FIG. 2 are photographs showing results of immunohistochemical staining using a monoclonal antibody obtained from the hybridoma cell line (accession number: NITE BP-02527). In each case, a magnification was 400 times.

(a) of FIG. 2 is a photograph showing a result of staining a tissue slice of a normal region of a patient suffering from a testicular tumor. Moreover, (b) of FIG. 2 is a photograph showing a result of staining a tissue slice of a seminoma which is a type of the testicular tumor. Furthermore, (c) of FIG. 2 is a photograph showing a result of staining a tissue slice of a normal region in a gastric tissue of a patient suffering from a gastric cancer. (d) of FIG. 2 is a photograph showing a result of staining a tissue slice of a tumor region in the gastric tissue of the patient suffering from the gastric cancer.

As a result, it was confirmed that the KK-LC-1 protein was stained in staining of all the tissue slices. From the result, it was found that the monoclonal antibody obtained from the hybridoma cell line (accession number: NITE BP-02527) has binding properties to the KK-LC-1 protein in the fixed biological sample. Furthermore, expression of a KK-LC-1 gene was positive in all the tissues of the tumor region and the normal region of the patient suffering from the gastric cancer, which were used in the present Experimental Example.

In addition, from the above results, it was found that even a monoclonal antibody having high reactivity in the ELISA method does not always show reactivity by immunohistochemical staining.

Experimental Example 4

(Confirmation 2 of Reactivity of Monoclonal Antibody by Immunohistochemical Staining)

The reactivity of the monoclonal antibody obtained from the hybridoma cell line (accession number: NITE BP-02527) was investigated. Specifically, the monoclonal antibody obtained from the hybridoma cell line (accession number: NITE BP-02527) was absorbed by the peptide used for the immunization of the mouse at the time of establishing the hybridoma cell line (accession number: NITE BP-02527), then immunohistochemical staining was performed in the same manner as in Experimental Example 3, and the reactivity was investigated. Moreover, for comparison, immunohistochemical staining was also performed using a monoclonal antibody which was not subjected to an absorption operation.

For the absorption operation of the monoclonal antibody, the peptide having the amino acid sequence set forth in SEQ ID NO: 1 was used at a final concentration of 0.05 mg/mL. Moreover, the absorption operation was performed overnight at 4° C.

(a) to (d) of FIG. 3 are photographs showing results of immunohistochemical staining. In each case, a magnification was 200 times. (a) and (b) of FIG. 3 are photographs showing results of staining a tissue slice of a tumor region in the gastric tissue of the patient suffering from the gastric cancer. (a) of FIG. 3 is a result of immunostaining using a monoclonal antibody which was not subjected to the absorption operation. Moreover, (b) of FIG. 3 is a result of immunostaining using a monoclonal antibody after the absorption operation.

In addition, (c) and (d) of FIG. 3 are photographs showing results of staining a tissue slice of a normal region in the gastric tissue of the patient suffering from the gastric cancer. (c) of FIG. 3 is a result of immunostaining using a monoclonal antibody which was not subjected to the absorption operation. Moreover, (d) of FIG. 3 is a result of immunostaining using a monoclonal antibody after the absorption operation.

As a result, it was found that in the monoclonal antibody subjected to the absorption operation, reactivity to KK-LC-1 is lost. The result indicates that the produced monoclonal antibody has specific reactivity to the KK-LC-1. Furthermore, expression of a KK-LC-1 gene was positive in all the tissues of the tumor region and the normal region of the patient suffering from the gastric cancer, which were used in the present Experimental Example.

Experimental Example 5

(Confirmation 3 of Reactivity of Monoclonal Antibody by Immunohistochemical Staining)

The reactivity of the monoclonal antibody obtained from the hybridoma cell line (accession number: NITE BP-02527) was further investigated. Specifically, by using the monoclonal antibody obtained from the hybridoma cell line (accession number: NITE BP-02527), immunohistochemical staining was performed in the same manner as in Experimental Example 3, and the reactivity was investigated. Here, as the tissue slice, a sample which was the normal region or the tumor region in the gastric tissue of the patient suffering from the gastric cancer and in which the expression of the KK-LC-1 gene was negative was used.

(a) to (c) of FIG. 4 are photographs showing results of immunohistochemical staining using a monoclonal antibody obtained from the hybridoma cell line (accession number: NITE BP-02527). In each case, a magnification was 400 times.

(a) of FIG. 4 is a photograph showing a result of staining a tissue slice which was the normal region in the gastric tissue of the patient suffering from the gastric cancer and in which the expression of the KK-LC-1 gene was negative. Moreover, (b) and (c) of FIG. 2 are photographs showing results of staining a tissue slice which was the tumor region in the gastric tissue of the patient suffering from the gastric cancer and in which the expression of the KK-LC-1 gene was negative.

As a result, the KK-LC-1 protein was not detected in staining of all the tissue slices. The result further supports that the monoclonal antibody obtained from the hybridoma cell line (accession number: NITE BP-02527) has specific reactivity to the KK-LC-1 in the fixed biological sample.

Experimental Example 6

(Confirmation 4 of Reactivity of Monoclonal Antibody by Immunohistochemical Staining)

The reactivity of the monoclonal antibody obtained from the hybridoma cell line (accession number: NITE BP-02527) was compared with reactivity of a commercially available anti-KK-LC-1 polyclonal antibody (model "HPA004773", Sigma-Aldrich Co. LLC).

Specifically, by using the monoclonal antibody (culture supernatant was diluted to 1/80) obtained from the hybridoma cell line (accession number: NITE BP-02527) and the commercially available anti-KK-LC-1 polyclonal antibody (model "HPA004773", Sigma-Aldrich Co. LLC, which is diluted to 1/50), immunohistochemical staining was performed in the same manner as in Experimental Example 3, and the reactivity was investigated. Here, as the tissue slice, a testis sample in which the KK-LC-1 gene was strongly expressed was used.

(a) and (b) of FIG. 5 are photographs showing results of immunohistochemical staining. In each case, a magnification was 400 times. (a) of FIG. 5 is a photograph showing a result of staining using the monoclonal antibody obtained from the hybridoma cell line (accession number: NITE BP-02527). Moreover, (b) of FIG. 5 is a photograph showing a result of staining using the commercially available anti-KK-LC-1 polyclonal antibody (model "HPA004773", Sigma-Aldrich Co. LLC).

As a result, it was found that in the monoclonal antibody obtained from the hybridoma cell line (accession number: NITE BP-02527), the KK-LC-1 in the fixed biological sample could be favorably detected, whereas in the commercially available anti-KK-LC-1 polyclonal antibody, the KK-LC-1 in the fixed biological sample could not be stained. The result shows usefulness of the monoclonal antibody obtained from the hybridoma cell line (accession number: NITE BP-02527).

Experimental Example 7

(Identification of Base Sequence and Amino Acid Sequence of Monoclonal Antibody)

The total RNA was prepared from the hybridoma cell line (accession number: NITE BP-02527), and reverse-transcribed to prepare cDNA. Subsequently, base sequences of an antibody heavy-chain variable region gene and an antibody light-chain variable region gene were sequenced by a conventional method.

The identified base sequence of the heavy-chain variable region gene is shown in SEQ ID NO: 10, and the identified base sequence of the light-chain variable region gene is shown in SEQ ID NO: 11. Moreover, an amino acid sequence of the heavy-chain variable region deduced from the base sequence is shown in SEQ ID NO: 8, and an amino acid sequence of the light-chain variable region deduced from the base sequence is shown in SEQ ID NO: 9.

In addition, an amino acid sequence of a heavy-chain CDR 1 is shown in SEQ ID NO: 2, an amino acid sequence of a heavy-chain CDR 2 is shown in SEQ ID NO: 3, and an amino acid sequence of a heavy-chain CDR 3 is shown in SEQ ID NO: 4. Furthermore, an amino acid sequence of a light-chain CDR 1 is shown in SEQ ID NO: 5, an amino acid sequence of a light-chain CDR 2 is shown in SEQ ID NO: 6, and an amino acid sequence of a light-chain CDR 3 is shown in SEQ ID NO: 7.

Experimental Example 8

(Analysis of Epitope Recognized by Monoclonal Antibodies)

An antigen of the monoclonal antibody produced by the hybridoma cell line (accession number: NITE BP-02527) was identified by epitope mapping. Specifically, first, 73 types of 15-amino acid residue peptides in which a position on an N-terminus side was shifted by one amino acid residue each were synthesized based on the amino acid sequence of the KK-LC-1 protein to produce a peptide array. Amino acid sequences of the 73 types of peptides are shown in SEQ ID NOs: 13 to 85, respectively.

Subsequently, the peptide array was reacted with a monoclonal antibody to identify peptides having reactivity. The monoclonal antibody was diluted to 1/100 and 1/500 and the resultants were each reacted.

FIG. 6 is a graph showing results of epitope mapping. As a result, it was found that the monoclonal antibody has binding properties to peptides around LSMVENKLVELEHTL (SEQ ID NO: 63) to VELEHTLLSKGFRGA (SEQ ID NO: 71).

As a result of identification of an amino acid sequence common to the peptides to which the monoclonal antibody was bound, it was found that an epitope of the monoclonal antibody is NKLVELEHTLLS (SEQ ID NO: 12). Furthermore, further investigation is required to determine whether or not the entire amino acid sequence set forth in SEQ ID NO: 12 is essential for binding to the monoclonal antibody. That is, the monoclonal antibody may have binding properties even to a peptide in which a serine residue at a C-terminus is deleted, a peptide in which an asparagine residue at an N-terminus is deleted, and a peptide in which the asparagine residue at the N-terminus and a second lysine residue from the N-terminus are deleted, in the amino acid sequence set forth in SEQ ID NO: 12.

INDUSTRIAL APPLICABILITY

According to the present invention, it is possible to provide a technique for easily detecting KK-LC-1. The present invention makes it possible to detect the expression of the KK-LC-1 by immunohistochemical staining, for example. Moreover, an anti-KK-LC-1 monoclonal antibody can be semipermanently supplied, and thus can be suitably used as a diagnostic agent.

Accession Number
    NITE BP-02527

The invention claimed is:

1. A monoclonal antibody or an antigen binding fragment thereof that binds Kitakyushu lung cancer antigen-I (KK-LC-1), wherein the antibody or antigen binding fragment thereof comprises: heavy-chain complementarity-determining regions (CDRs) 1 to 3 that respectively consist of amino acid sequences of SEQ ID NOs: 2 to 4 and light-chain CDRs 1 to 3 that respectively consist of amino acid sequences of SEQ ID NOs: 5 to 7.

2. The monoclonal antibody or antigen binding fragment thereof according to claim 1, wherein the monoclonal antibody or the antigen binding fragment thereof is capable of histological staining the KK-LC-1 protein present in a fixed biological sample, wherein KK-LC-1 protein comprises the amino acid sequence of SEQ ID NO: 1.

3. The monoclonal antibody or the antigen binding fragment thereof according to claim 2, wherein the biological sample is fixed with a crosslinking fixative.

4. The monoclonal antibody or the antigen binding fragment thereof according to claim 3, wherein the crosslinking fixative is formaldehyde, paraformaldehyde, or glutaraldehyde.

5. The monoclonal antibody or the antigen binding fragment thereof according to claim 1, wherein the monoclonal antibody or the antigen binding fragment thereof has binding properties to the peptide consisting of the amino acid sequence set forth in SEQ ID NO: 1.

6. The monoclonal antibody or the antigen binding fragment thereof according to claim 1, wherein the monoclonal antibody or the antigen binding fragment thereof has binding properties to the peptide consisting of the amino acid sequence set forth in SEQ ID NO: 12.

7. The monoclonal antibody according claim 1, wherein the monoclonal antibody is produced by a hybridoma cell line having an accession number of NITE BP-02527.

8. A detection kit comprising the monoclonal antibody or the antigen binding fragment thereof according to claim 1.

9. A nucleic acid encoding the monoclonal antibody or the antigen binding fragment thereof as set forth in claim 1.

10. A hybridoma cell line deposited at the National Institute of Technology and Evaluation under accession number NITE BP-02527.

11. An immunohistochemical method for detecting a KK-LC-1 protein comprising the amino acid sequence of SEQ ID NO: 1, in a biological sample, the method comprising a step of detecting the peptide consisting of an amino acid sequence set forth in SEQ ID NO: 1 or a partial peptide thereof, wherein the partial peptide is the peptide consisting of an amino acid sequence set forth in SEQ ID NO: 12, by contacting the sample with the monoclonal antibody or the antigen binding fragment thereof of claim 1.

* * * * *